(12) United States Patent
Cady

(10) Patent No.: US 11,938,018 B2
(45) Date of Patent: *Mar. 26, 2024

(54) INTRAOCULAR PSEUDOPHAKIC CONTACT LENS (IOPCL) FOR TREATING AGE-RELATED MACULAR DEGENERATION (AMD) OR OTHER EYE DISORDERS

(71) Applicant: OnPoint Vision, Inc., Aliso Viejo, CA (US)

(72) Inventor: Kevin J. Cady, Laguna Hills, CA (US)

(73) Assignee: OnPoint Vision, Inc., Aliso Viejo, CA (US)

(*) Notice: Subject to any disclaimer, the term of this patent is extended or adjusted under 35 U.S.C. 154(b) by 562 days.

This patent is subject to a terminal disclaimer.

(21) Appl. No.: 17/332,577

(22) Filed: May 27, 2021

(65) Prior Publication Data

US 2021/0282920 A1 Sep. 16, 2021

Related U.S. Application Data

(63) Continuation-in-part of application No. 17/011,975, filed on Sep. 3, 2020, now Pat. No. 11,432,921, and (Continued)

(51) Int. Cl.
*A61F 2/16* (2006.01)
*A61F 9/00* (2006.01)

(52) U.S. Cl.
CPC .......... *A61F 2/1602* (2013.01); *A61F 2/1648* (2013.01); *A61F 2002/1681* (2013.01); (Continued)

(58) Field of Classification Search
CPC ...... A61F 2/1602; A61F 2/161; A61F 2/1694; A61F 2/1613; A61F 2/1648; (Continued)

(56) References Cited

U.S. PATENT DOCUMENTS 4,124,905 A 11/1978 Clark
4,932,971 A * 6/1990 Kelman ................ A61F 2/1648
623/6.34
(Continued)

FOREIGN PATENT DOCUMENTS

AU 2014202532 A1 7/2014
BR PI1005015 A2 4/2013
(Continued)

OTHER PUBLICATIONS

Grant of Patent dated Jan. 17, 2022 in connection with Korean Patent Application No. 10-2021-7018671, 7 pages.
(Continued)

*Primary Examiner* — Javier G Blanco

(57) ABSTRACT

An apparatus includes an intraocular pseudophakic contact lens having an optical lens and haptics extending radially from the optical lens and configured to contact a capsular bag in an eye in order to secure the intraocular pseudophakic contact lens against an artificial intraocular lens. The optical lens includes a central portion and at least one annular portion surrounding the central portion, where the central and annular portions are configured to provide different optical powers. The central portion of the optical lens may be configured to provide an optical magnification, and the at least one annular portion of the optical lens may be configured to provide at least one different optical magnification or no optical magnification.

20 Claims, 8 Drawing Sheets

Related U.S. Application Data a continuation-in-part of application No. 16/717,304, filed on Dec. 17, 2019, now Pat. No. 11,109,957, which is a continuation-in-part of application No. 16/398,627, filed on Apr. 30, 2019, now Pat. No. 10,945,832, said application No. 17/011,975 is a continuation of application No. 16/190,959, filed on Nov. 14, 2018, now Pat. No. 10,842,614, said application No. 16/398,627 is a continuation-in-part of application No. 15/646,254, filed on Jul. 11, 2017, now Pat. No. 10,299,910, said application No. 16/190,959 is a continuation of application No. 14/860,629, filed on Sep. 21, 2015, now Pat. No. 10,159,562, said application No. 15/646,254 is a continuation-in-part of application No. 14/860,629, filed on Sep. 21, 2015, now Pat. No. 10,159,562.

(60) Provisional application No. 63/057,738, filed on Jul. 28, 2020, provisional application No. 62/053,771, filed on Sep. 22, 2014.

(52) U.S. Cl.
CPC ... *A61F 2002/16902* (2015.04); *A61F 2/1694* (2013.01); *A61F 9/0017* (2013.01); *A61F 2220/0016* (2013.01)

(58) Field of Classification Search
CPC .... A61F 2002/16902; A61F 2002/1681; A61F 2002/1689; A61F 2002/169; A61F 2220/0025; A61F 2220/0016
See application file for complete search history.

(56) References Cited

U.S. PATENT DOCUMENTS

| | | |
|---|---|---|
| 5,071,432 A | 12/1991 | Baikoff |
| 5,078,742 A | 1/1992 | Dahan |
| 5,098,444 A | 3/1992 | Feaster |
| 5,133,747 A | 7/1992 | Feaster |
| 5,201,762 A | 4/1993 | Hauber |
| 5,217,491 A | 6/1993 | Vanderbilt |
| 5,266,241 A | 11/1993 | Parekh |
| 5,275,623 A | 1/1994 | Sarfarazi |
| 5,354,334 A | 10/1994 | Fedorov et al. |
| 5,358,520 A | 10/1994 | Patel |
| 5,443,506 A | 8/1995 | Garabet |
| 5,443,507 A | 8/1995 | Jacobi |
| 5,522,891 A | 6/1996 | Klaas |
| 5,539,016 A | 7/1996 | Kunzier et al. |
| 5,684,560 A | 11/1997 | Roffman et al. |
| 5,693,095 A | 12/1997 | Freeman et al. |
| 5,699,142 A | 12/1997 | Lee et al. |
| 5,728,156 A | 3/1998 | Gupta |
| 5,755,786 A | 5/1998 | Woffinden et al. |
| 5,769,890 A | 6/1998 | McDonald |
| 5,782,911 A | 7/1998 | Herrick |
| 5,814,103 A | 9/1998 | Lipshitz et al. |
| 5,824,074 A | 10/1998 | Koch |
| 6,027,531 A | 2/2000 | Tassignon |
| 6,030,416 A | 2/2000 | Huo et al. |
| 6,045,577 A | 4/2000 | Woffinden et al. |
| 6,113,633 A | 9/2000 | Portney |
| 6,142,625 A | 11/2000 | Sawano et al. |
| 6,169,127 B1 | 1/2001 | Lohmann et al. |
| 6,197,057 B1 | 3/2001 | Peyman et al. |
| 6,200,342 B1 | 3/2001 | Tassignon |
| 6,217,171 B1 | 4/2001 | Auten et al. |
| 6,217,612 B1 | 4/2001 | Woods |
| 6,197,058 B1 | 6/2001 | Portney |
| 6,277,146 B1 | 8/2001 | Peyman et al. |
| 6,419,697 B1 | 7/2002 | Kelman |
| 6,454,801 B1 | 9/2002 | Portney |
| 6,464,725 B2 | 10/2002 | Skotton |
| 6,488,708 B2 | 12/2002 | Sarfarazi |
| 6,554,859 B1 | 4/2003 | Lang et al. |
| 6,554,860 B2 | 4/2003 | Hoffmann et al. |
| 6,558,420 B2 | 5/2003 | Green |
| 6,582,076 B1 | 6/2003 | Roffman et al. |
| 6,616,691 B1 | 9/2003 | Tran |
| 6,616,692 B1 | 9/2003 | Glick et al. |
| 6,645,246 B1 | 11/2003 | Weinschenk, III et al. |
| 6,705,729 B2 | 3/2004 | Piers et al. |
| 6,749,634 B2 | 6/2004 | Hanna |
| 6,767,363 B1 | 7/2004 | Bandhauer et al. |
| 6,797,004 B1 | 9/2004 | Brady et al. |
| 6,818,017 B1 | 11/2004 | Shu |
| 6,827,738 B2 | 12/2004 | Willis et al. |
| 6,851,803 B2 | 2/2005 | Wooley et al. |
| 6,860,601 B2 | 3/2005 | Shadduck |
| 6,880,558 B2 | 4/2005 | Perez |
| 6,926,736 B2 | 8/2005 | Peng et al. |
| 6,952,313 B2 | 10/2005 | Schrader |
| 6,960,230 B2 | 11/2005 | Haefliger |
| 6,960,231 B2 | 11/2005 | Tran |
| 6,991,651 B2 | 1/2006 | Portney |
| 7,008,448 B2 | 3/2006 | Lipshitz et al. |
| 7,008,449 B2 | 3/2006 | Willis et al. |
| 7,029,497 B2 | 4/2006 | Zhang et al. |
| 7,036,931 B2 | 5/2006 | Lindacher et al. |
| 7,081,134 B2 | 7/2006 | Cukrowski |
| 7,101,397 B2 | 9/2006 | Aharoni |
| 7,111,938 B2 | 9/2006 | Andino et al. |
| 7,118,597 B2 | 10/2006 | Miller et al. |
| 7,150,760 B2 | 12/2006 | Zhang |
| 7,186,266 B2 | 3/2007 | Peyman |
| 7,220,278 B2 | 5/2007 | Peyman |
| 7,223,288 B2 | 5/2007 | Zhang et al. |
| 7,238,201 B2 | 6/2007 | Portney et al. |
| 7,279,006 B2 | 10/2007 | Vincent |
| 7,311,194 B2 | 12/2007 | Jin et al. |
| 7,316,713 B2 | 1/2008 | Zhang |
| 7,338,161 B2 | 3/2008 | Chauveau et al. |
| 7,452,378 B2 | 11/2008 | Zadno-Azizi et al. |
| 7,453,646 B2 | 11/2008 | Lo |
| 7,462,193 B2 | 12/2008 | Nagamoto |
| 7,572,007 B2 | 8/2009 | Simpson |
| 7,591,849 B2 | 9/2009 | Richardson |
| 7,604,349 B2 | 10/2009 | Blum et al. |
| 7,744,647 B2 | 6/2010 | Barrett |
| 7,794,498 B2 | 9/2010 | Pinchuk |
| 7,806,929 B2 | 10/2010 | Brown |
| 7,842,087 B2 | 11/2010 | Ben Nun |
| 7,871,162 B2 | 1/2011 | Weeber |
| 7,871,437 B2 | 1/2011 | Hermans et al. |
| 7,875,661 B2 | 1/2011 | Salamone |
| 7,892,264 B2 | 2/2011 | Sanders et al. |
| 7,905,917 B2 | 3/2011 | Altmann |
| 7,918,886 B2 | 4/2011 | Aharoni et al. |
| 7,942,929 B2 | 5/2011 | Linhardt et al. |
| 7,955,704 B2 | 6/2011 | Lowery et al. |
| 8,012,204 B2 | 9/2011 | Weinschenk, III et al. |
| 8,034,107 B2 | 10/2011 | Stenger |
| 8,109,999 B2 | 2/2012 | Hampp |
| 8,133,274 B2 | 3/2012 | Zhou et al. |
| 8,197,541 B2 | 6/2012 | Schedler |
| 8,222,360 B2 | 7/2012 | Liao |
| 8,231,219 B2 | 7/2012 | Weeber |
| 8,273,123 B2 | 9/2012 | Ben Nun |
| 8,324,256 B2 | 12/2012 | Domschke et al. |
| 8,337,552 B2 | 12/2012 | Kobayashi et al. |
| 8,377,124 B2 | 2/2013 | Hong et al. |
| 8,419,791 B2 | 4/2013 | Toop |
| 8,430,928 B2 | 4/2013 | Liao |
| 8,491,651 B2 | 7/2013 | Tsai et al. |
| 8,523,942 B2 | 9/2013 | Cumming |
| 8,530,590 B2 | 9/2013 | Hu et al. |
| 8,579,972 B2 | 11/2013 | Rombach |
| 8,603,167 B2 | 12/2013 | Rombach |
| 8,608,799 B2 | 12/2013 | Blake |
| 8,636,358 B2 | 1/2014 | Binder |
| 8,680,172 B2 | 3/2014 | Liao |

(56) References Cited

U.S. PATENT DOCUMENTS

| | | | |
|---|---|---|---|
| 8,696,746 B2 | 4/2014 | Wanders et al. |
| 8,834,566 B1 | 9/2014 | Jones |
| 8,852,274 B2 | 10/2014 | Doraiswamy et al. |
| 8,858,626 B2 | 10/2014 | Noy |
| 8,920,495 B2 | 12/2014 | Mirlay |
| 8,945,213 B2 | 2/2015 | Terwee et al. |
| 8,968,399 B2 | 3/2015 | Ghabra |
| 8,992,611 B2 | 3/2015 | Zhao |
| D729,390 S | 5/2015 | Doraiswamy et al. |
| 9,039,760 B2 | 5/2015 | Brady et al. |
| 9,072,600 B2 | 7/2015 | Tran |
| 9,084,674 B2 | 7/2015 | Brady et al. |
| D738,947 S | 9/2015 | Litovchenko |
| 9,237,946 B2 | 1/2016 | Pynson |
| 9,304,329 B2 | 4/2016 | Zhao |
| 9,329,410 B2 | 5/2016 | Riall et al. |
| 9,387,069 B2 | 7/2016 | Kahook et al. |
| 9,445,892 B2 | 9/2016 | Brown |
| 9,554,893 B2 | 1/2017 | Brady et al. |
| 9,675,445 B2 | 6/2017 | Moriarty |
| 9,757,228 B2 | 9/2017 | Wanders et al. |
| 9,808,339 B2 | 11/2017 | Dorronsoro Diaz et al. |
| 9,820,849 B2 | 11/2017 | Jansen |
| 9,848,980 B2 | 12/2017 | McCafferty |
| 9,869,885 B2 | 1/2018 | De Sio et al. |
| 9,931,202 B2 | 4/2018 | Borja et al. |
| 9,937,034 B2 | 4/2018 | Wanders |
| 10,004,592 B2 | 6/2018 | Amon |
| 10,004,596 B2 | 6/2018 | Brady et al. |
| 10,028,824 B2 | 7/2018 | Kahook et al. |
| 10,299,910 B2 | 5/2019 | Cady |
| 10,842,614 B2 | 11/2020 | Cady |
| 11,083,622 B2 | 8/2021 | Cady et al. |
| 11,109,957 B2 | 9/2021 | Cady |
| 2002/0120329 A1 | 8/2002 | Lang et al. |
| 2002/0161436 A1 | 10/2002 | Portney |
| 2003/0158560 A1 | 8/2003 | Portney |
| 2003/0187504 A1 | 10/2003 | Weinschenk, III et al. |
| 2003/0220687 A1 | 11/2003 | Nordan et al. |
| 2004/0106993 A1 | 6/2004 | Portney |
| 2004/0158322 A1 | 8/2004 | Shen |
| 2004/0167621 A1 | 8/2004 | Peyman |
| 2004/0236422 A1 | 11/2004 | Zhang et al. |
| 2004/0249455 A1 | 12/2004 | Tran |
| 2005/0027354 A1 | 2/2005 | Brady et al. |
| 2005/0060032 A1 | 3/2005 | Magnante et al. |
| 2005/0113913 A1 | 5/2005 | Duvert |
| 2006/0001186 A1 | 1/2006 | Richardson et al. |
| 2006/0047339 A1 | 3/2006 | Brown |
| 2006/0058874 A1 | 3/2006 | Peli |
| 2006/0142856 A1 | 6/2006 | Willis et al. |
| 2006/0184244 A1 | 8/2006 | Nguyen et al. |
| 2006/0241752 A1 | 10/2006 | Israel |
| 2006/0253196 A1 | 11/2006 | Woods |
| 2006/0265059 A1 | 11/2006 | Sunada et al. |
| 2007/0010881 A1 | 1/2007 | Soye et al. |
| 2007/0016293 A1 | 1/2007 | Tran |
| 2007/0021832 A1 | 1/2007 | Nordan |
| 2007/0032866 A1 | 2/2007 | Portney |
| 2007/0118216 A1 | 5/2007 | Pynson |
| 2007/0260308 A1 | 11/2007 | Tran |
| 2007/0260309 A1 | 11/2007 | Richardson |
| 2007/0270947 A1 | 11/2007 | Peyman |
| 2007/0282438 A1 | 12/2007 | Hong et al. |
| 2008/0046077 A1 | 2/2008 | Cumming |
| 2008/0051886 A1 | 2/2008 | Lin |
| 2008/0086208 A1 | 4/2008 | Nordan |
| 2008/0103592 A1 | 5/2008 | Maloney |
| 2008/0147085 A1 | 6/2008 | Gardeski et al. |
| 2008/0208334 A1 | 8/2008 | Jinkerson et al. |
| 2008/0208335 A1 | 8/2008 | Blum |
| 2008/0215147 A1 | 9/2008 | Werblin |
| 2008/0281414 A1 | 11/2008 | Akahoshi |
| 2008/0288066 A1 | 11/2008 | Cumming |
| 2008/0312738 A1 | 12/2008 | Wanders |
| 2009/0048671 A1 | 2/2009 | Lipshitz et al. |
| 2009/0062911 A1 | 3/2009 | Bogaert |
| 2009/0130176 A1 | 5/2009 | Bossy-Nobs et al. |
| 2009/0182422 A1 | 7/2009 | Nordan et al. |
| 2009/0198326 A1 | 8/2009 | Zhou et al. |
| 2010/0004742 A1 | 1/2010 | Cumming |
| 2010/0016965 A1 | 1/2010 | Hong et al. |
| 2010/0036488 A1 | 2/2010 | de Juan, Jr. et al. |
| 2010/0094412 A1 | 4/2010 | Wensrich |
| 2010/0094413 A1 | 4/2010 | Rombach et al. |
| 2010/0131061 A1 | 5/2010 | Callahan et al. |
| 2010/0161048 A1 | 6/2010 | Schaper, Jr. |
| 2010/0161050 A1 | 6/2010 | Detmers et al. |
| 2010/0211171 A1 | 8/2010 | Sarfarazi |
| 2010/0280609 A1 | 11/2010 | Simonov et al. |
| 2010/0292789 A1 | 11/2010 | Willis et al. |
| 2011/0021733 A1 | 1/2011 | Wanders et al. |
| 2011/0153014 A1 | 6/2011 | Zhang et al. |
| 2011/0251686 A1 | 10/2011 | Masket |
| 2011/0313520 A1 | 12/2011 | Shoji et al. |
| 2011/0313521 A1 | 12/2011 | Angelopoulos |
| 2011/0313522 A1 | 12/2011 | Hayes |
| 2011/0313523 A1 | 12/2011 | Hayes |
| 2012/0109294 A1 | 5/2012 | Olson |
| 2012/0232649 A1 | 9/2012 | Cuevas |
| 2012/0253459 A1 | 10/2012 | Reich et al. |
| 2012/0323321 A1 | 12/2012 | Simonov et al. |
| 2013/0066422 A1 | 3/2013 | Dworschak et al. |
| 2013/0110234 A1 | 5/2013 | DeVita et al. |
| 2013/0110235 A1 | 5/2013 | Schwiegerling |
| 2013/0131796 A1 | 5/2013 | Mirlay |
| 2013/0190868 A1 | 7/2013 | Kahook et al. |
| 2013/0197636 A1 | 8/2013 | Haefliger |
| 2013/0204364 A1 | 8/2013 | Olson |
| 2013/0238091 A1 | 9/2013 | Danta et al. |
| 2013/0253159 A1 | 9/2013 | Benz et al. |
| 2013/0304206 A1 | 11/2013 | Pallikaris et al. |
| 2013/0317607 A1 | 11/2013 | Deboer et al. |
| 2013/0338767 A1 | 12/2013 | Mazzocchi et al. |
| 2014/0052246 A1 | 2/2014 | Kahook et al. |
| 2014/0058507 A1 | 2/2014 | Reich et al. |
| 2014/0121768 A1 | 5/2014 | Simpson |
| 2014/0180404 A1 | 6/2014 | Tran |
| 2014/0180406 A1 | 6/2014 | Simpson |
| 2014/0228949 A1 | 8/2014 | Argento et al. |
| 2014/0240657 A1 | 8/2014 | Pugh et al. |
| 2014/0243972 A1 | 8/2014 | Wanders |
| 2014/0253877 A1 | 9/2014 | Li et al. |
| 2014/0277434 A1 | 9/2014 | Weeber et al. |
| 2014/0330375 A1 | 11/2014 | McCafferty |
| 2014/0330376 A1 | 11/2014 | Kleinman |
| 2014/0347624 A1 | 11/2014 | Ando et al. |
| 2014/0368789 A1 | 12/2014 | Webb |
| 2015/0230981 A1 | 8/2015 | Kahook et al. |
| 2015/0297342 A1 | 10/2015 | Rosen et al. |
| 2016/0000558 A1 | 1/2016 | Honigsbaum |
| 2016/0008126 A1 | 1/2016 | Salahieh et al. |
| 2016/0081791 A1 | 3/2016 | Cady |
| 2016/0199176 A1* | 7/2016 | Wanders ............... A61F 2/1648 623/6.34 |
| 2016/0256265 A1 | 9/2016 | Borja et al. |
| 2016/0317286 A1 | 11/2016 | Brady et al. |
| 2016/0334643 A1 | 11/2016 | Hyde et al. |
| 2017/0172733 A1 | 6/2017 | Scharioth et al. |
| 2017/0296331 A1 | 10/2017 | Werblin et al. |
| 2017/0304045 A1 | 10/2017 | Cady |
| 2019/0254808 A1 | 8/2019 | Cady |
| 2020/0397562 A1 | 12/2020 | Cady |
| 2021/0186681 A1 | 6/2021 | Qureshi et al. |
| 2021/0290369 A1 | 9/2021 | Cady |

FOREIGN PATENT DOCUMENTS

| | | |
|---|---|---|
| BR | 102012000755 A2 | 10/2013 |
| CN | 2717403 Y | 8/2005 |
| CN | 201015617 Y | 2/2008 |
| CN | 203425064 U | 2/2014 |
| DE | 19501444 A1 | 7/1996 |
| DE | 20109306 U1 | 8/2001 |

(56) References Cited

FOREIGN PATENT DOCUMENTS

| | | |
|---|---|---|
| DE | 10025320 A1 | 11/2001 |
| DE | 102007002885 A1 | 7/2008 |
| DE | 202010002895 U1 | 5/2010 |
| DE | 202013009162 U1 | 11/2013 |
| EP | 0760232 A1 | 3/1997 |
| EP | 1369710 A2 | 12/2003 |
| EP | 1449498 A2 | 8/2004 |
| EP | 1493405 A1 | 1/2005 |
| EP | 1504730 A1 | 2/2005 |
| EP | 1658828 A1 | 5/2006 |
| FR | 2666735 A1 | 3/1992 |
| FR | 2869793 A1 | 11/2005 |
| FR | 2966340 A1 | 4/2012 |
| FR | 2998474 A1 | 5/2014 |
| GB | 2464505 A | 4/2010 |
| GB | 2517531 A | 2/2015 |
| JP | H07255757 A | 10/1995 |
| JP | 2002360616 A | 12/2002 |
| JP | 2004528065 A | 9/2004 |
| JP | 4199573 B2 | 10/2004 |
| JP | 2006511242 A | 4/2006 |
| JP | 4363573 B2 | 11/2009 |
| JP | 4431372 B2 | 3/2010 |
| JP | 5398089 B2 | 6/2013 |
| JP | 2013528098 A | 7/2013 |
| JP | 5383782 B2 | 1/2014 |
| JP | 2016534816 A | 11/2016 |
| JP | 2017528300 A | 9/2017 |
| JP | 2020526336 A | 8/2020 |
| KR | 101555298 B1 | 9/2015 |
| KR | 102569508 B1 | 8/2023 |
| RU | 2045246 C1 | 10/1995 |
| RU | 2080100 C1 | 8/1996 |
| RU | 2070004 C1 | 12/1996 |
| RU | 2129880 C1 | 5/1999 |
| RU | 2134086 C1 | 8/1999 |
| RU | 31954 U1 | 9/2003 |
| RU | 2234417 C2 | 8/2004 |
| RU | 47696 U1 | 9/2005 |
| RU | 2281063 C1 | 8/2006 |
| RU | 2281067 C1 | 8/2006 |
| RU | 2281726 C1 | 8/2006 |
| RU | 2283067 C1 | 9/2006 |
| RU | 2288494 C2 | 11/2006 |
| RU | 2377964 C2 | 1/2010 |
| RU | 2457811 C1 | 8/2012 |
| RU | 2479286 C1 | 4/2013 |
| RU | 2531472 C1 | 10/2014 |
| TW | M329428 U | 4/2008 |
| TW | 201103517 A | 2/2011 |
| WO | 8909576 A1 | 10/1989 |
| WO | 91/13597 A1 | 9/1991 |
| WO | 92/15260 A1 | 9/1992 |
| WO | 94/07435 A1 | 4/1994 |
| WO | 94/13225 A1 | 6/1994 |
| WO | 96/05047 A1 | 2/1996 |
| WO | 97/12564 A1 | 4/1997 |
| WO | 99/18457 A2 | 4/1999 |
| WO | 99/35520 A1 | 7/1999 |
| WO | 99/56671 A1 | 11/1999 |
| WO | 99/62434 A1 | 12/1999 |
| WO | 00/48491 A1 | 8/2000 |
| WO | 01/08605 A1 | 2/2001 |
| WO | 01/15635 A1 | 3/2001 |
| WO | 01/87182 A2 | 11/2001 |
| WO | 2005/104994 A2 | 11/2005 |
| WO | 2006/025726 A1 | 3/2006 |
| WO | 2006/119016 A2 | 11/2006 |
| WO | 2007/138564 A1 | 12/2007 |
| WO | 2008/094518 A1 | 8/2008 |
| WO | 2010095938 A1 | 8/2010 |
| WO | 2010/131955 A1 | 11/2010 |
| WO | 2011/115860 A2 | 9/2011 |
| WO | 2012054402 A2 | 4/2012 |
| WO | 2013/055212 A1 | 4/2013 |
| WO | 2013/169652 A2 | 11/2013 |
| WO | 2014/058315 A1 | 4/2014 |
| WO | 2014/058316 A1 | 4/2014 |
| WO | 2014/071532 A1 | 5/2014 |
| WO | 2014/099338 A1 | 6/2014 |
| WO | 2014/108100 A1 | 7/2014 |
| WO | 2015/006839 A1 | 1/2015 |
| WO | 2015/022514 A1 | 2/2015 |
| WO | 2015/026226 A1 | 2/2015 |
| WO | 2015/037994 A1 | 3/2015 |
| WO | 2015/044235 A1 | 4/2015 |
| WO | 2015/066502 A1 | 5/2015 |

OTHER PUBLICATIONS

"1/1-Designs—Questel", May 2018, 3 pages.
"1/1-Designs—Questel", May 2018, 4 pages.
Extended European Search Report and Written Opinion for European U.S. Appl. No. 15/845,158 dated Mar. 6, 2018, 9 pages.
International Search Report and Written Opinion of the International Searching Authority dated Aug. 30, 2018 in connection with International Patent Application No. PCT/US2018/36519, 13 pages.
International Search Report and Written Opinion of the International Searching Authority dated Dec. 21, 2015 in connection with International Patent Application No. PCT/US2015/051415, 9 pages.
Office Action dated Jun. 24, 2019 in connection with New Zealand Patent Application No. 729994, 3 pages.
Office Action dated Aug. 1, 2019 in connection with Japanese Patent Application No. 2017-535622, 11 pages.
Office Action in connection with Australian Patent Application No. 2019204613 dated Nov. 22, 2019, 3 pages.
Office Action dated Jul. 29, 2020 in connection with Australian Patent Application No. 2019204613, 3 pages.
Office Action dated May 20, 2020 in connection with Australian Patent Application No. 2018301248, 3 pages.
Communication pursuant to Article 94(3) EPC dated Jul. 15, 2020 in connection with European Patent Application No. 15845158.3, 6 pages.
Office Action dated Aug. 3, 2020 in connection with U.S. Appl. No. 16/398,627, 78 pages.
Supplementary European Search Report dated Oct. 28, 2020 in connection with European Patent Application No. 18831320, 7 pages.
Communication pursuant to Rules 70(2) and 70a(2) EPC dated Nov. 17, 2020 in connection with European Patent Application No. 18831320, 1 page.
Office Action dated Jan. 5, 2021 in connection with Japanese Patent Application No. 2020-066515, 4 pages.
Office Action dated Mar. 19, 2020 in connection with U.S. Appl. No. 16/190,959, 81 pages.
Cady et al., "Intraocular Pseudophakic Contact Lens (IOPCL)-Based Telescopic Approach for Treating Age-Related Macular Degeneration (AMD) or Other Eye Disorders", U.S. Appl. No. 17/332,533, filed May 27, 2021, 35 pages.
Examination Report dated Mar. 31, 2021 in connection with New Zealand Patent Application No. 755995, 3 pages.
Office Action dated Apr. 2, 2021 in connection with Chinese Patent Application No. 201880046413.X, 9 pages.
Notice of acceptance for patent application dated May 7, 2021 in connection with Australian Patent Application No. 2018301248, 31 pages.
Office Action dated Jul. 12, 2021 in connection with Australian Patent Application No. 2020239672, 4 pages.
European Search Report dated Jul. 16, 2021 in connection with European Patent Application No. 21161655.2, 5 pages.
Office Action dated Aug. 11, 2021 in connection with Australian Patent Application No. 2021200835, 2 pages.
Office Action dated Oct. 22, 2021 in connection with Canadian Patent Application No. 2,961,543, 5 pages.
Notice of Request for Submission of Argument dated Aug. 24, 2021 in connection with Korean Patent Application No. 10-2021-7018671, 12 pages.

(56) References Cited

OTHER PUBLICATIONS

European Search Report dated Sep. 2, 2021 in connection with European Patent Application No. 21168724, 7 pages.
International Search Report and Written Opinion of the International Searching Authority dated Oct. 7, 2021 in connection with International Patent Application No. PCT/US2021/037911, 9 pages.
Office Action dated Sep. 26, 2023 in connection with Korean Patent Application No. 10-2023-7028004, 29 pages.
Office Action dated Jul. 18, 2023 in connection with Japanese Patent Application No. 2022-170709, 7 pages.
Supplementary European Search Report dated Dec. 5, 2023 in connection with European Patent Application No. 20902943.8, 11 pages.
Examination Report No. 1 for Australian Patent Application No. AU2021245264 dated Sep. 20, 2022, 4 pages.
Examination Report No. 2 for Australian Patent Application No. AU2021245264 dated Nov. 23, 2022, 3 pages.
Decision to Grant a Patent for Japanese Patent Application No. 2021085035 dated Dec. 7, 2022, 4 pages.
Decision to Grant a Patent for Japanese Patent Application No. 2020501359 dated Nov. 29, 2022, 3 pages.
International Search Report dated Feb. 17, 2021 in connection with International Patent Application No. PCT/US2020/61099, 3 pages.
Written Opinion of the International Searching Authority dated Feb. 17, 2021 in connection with International Patent Application No. PCT/US2020/61099, 6 pages.
Japanese Patent Office, Office Action dated May 25, 2022 in connection with Japanese Patent Application No. 2021-085035, 4 pages.
Japanese Patent Office, Office Action dated Jul. 20, 2022 in connection with Japanese Patent Application No. 2020-501359, 4 pages.
Office Action dated Jan. 3, 2022 in connection with U.S. Appl. No. 17/011,975, 20 pages.
Office Action dated Oct. 12, 2021 in connection with Mexican Patent Application No. MX/a/2017/003760, 7 pages.

\* cited by examiner ic

INTRAOCULAR PSEUDOPHAKIC CONTACT LENS (IOPCL) FOR TREATING AGE-RELATED MACULAR DEGENERATION (AMD) OR OTHER EYE DISORDERS

CROSS-REFERENCE TO RELATED APPLICATIONS AND PRIORITY CLAIM

This application claims priority under 35 U.S.C. § 119(e) to U.S. Provisional Patent Application No. 63/057,738 filed on Jul. 28, 2020.

This application also claims priority under 35 U.S.C. § 120 as a continuation-in-part of U.S. patent application Ser. No. 17/011,975 filed on Sep. 3, 2020, which is a continuation of U.S. patent application Ser. No. 16/190,959 filed on Nov. 14, 2018 (now U.S. Pat. No. 10,842,614), which is a continuation of U.S. patent application Ser. No. 14/860,629 filed on Sep. 21, 2015 (now U.S. Pat. No. 10,159,562), which claims priority under U.S.C. § 119(e) to U.S. Provisional Patent Application No. 62/053,771 filed on Sep. 22, 2014.

This application further claims priority under 35 U.S.C. § 120 as a continuation-in-part of U.S. patent application Ser. No. 16/717,304 filed on Dec. 17, 2019, which is a continuation-in-part of U.S. patent application Ser. No. 16/398,627 filed on Apr. 30, 2019 (now U.S. Pat. No. 10,945,832), which is a continuation-in-part of U.S. patent application Ser. No. 15/646,254 filed on Jul. 11, 2017 (now U.S. Pat. No. 10,299,910), which is a continuation-in-part of U.S. patent application Ser. No. 14/860,629 filed on Sep. 21, 2015 (now U.S. Pat. No. 10,159,562), which claims priority under 35 U.S.C. § 119(e) to U.S. Provisional Patent Application No. 62/053,771 filed on Sep. 22, 2014.

All of these applications are hereby incorporated by reference in their entirety.

TECHNICAL FIELD

This disclosure relates generally to optical systems. More specifically, this disclosure relates to an intraocular pseudophakic contact lens (IOPCL) for treating age-related macular degeneration (AMD) or other eye disorders.

BACKGROUND

Age-related macular degeneration (AMD) causes deterioration of the macula in the retina of an eye. The retina is a paper-thin tissue at the back of the eye where light-sensitive cells send visual signals to the brain, and the macula supports finely-detailed vision. Sharp, clear, straight-ahead vision is centered in the macula, and damage to the macula results in central blind spots of various sizes and blurred or distorted central vision. Those affected by AMD find many daily activities, such as driving and reading, increasingly difficult and eventually impossible as the disease progresses. Common difficulties and symptoms of AMD include loss of ability to drive a car, loss of ability to read, distortion or loss of central vision, progressive decrease in contrast sensitivity, increase in glare and light sensitivity, need for increased illumination to read, and impaired depth perception.

AMD is the leading cause of visual impairment and irreversible vision loss in the United States. AMD is more prevalent among people 50 years of age or older, and it is one of the leading causes of legal blindness. As many as 15 million Americans currently have some type of AMD, including both early and intermediate stages. This number is expected to increase to nearly 22 million by 2050. Worldwide, it is estimated that more than 196 million people suffer from some level of AMD and that this number will increase to 288 million by 2040. Risk factors for developing AMD include positive family history, cigarette smoking, hyperopia, lightly-pigmented eye population, hypertension, and cardiovascular disease.

SUMMARY

This disclosure provides an intraocular pseudophakic contact lens (IOPCL) for treating age-related macular degeneration (AMD) or other eye disorders.

In a first embodiment, an apparatus includes an intraocular pseudophakic contact lens having an optical lens and haptics extending radially from the optical lens and configured to contact a capsular bag in an eye in order to secure the intraocular pseudophakic contact lens against an artificial intraocular lens. The optical lens includes a central portion and at least one annular portion surrounding the central portion, where the central and annular portions are configured to provide different optical powers.

In a second embodiment, a system includes an artificial intraocular lens having a first optical lens and first haptics configured to be implanted within a capsular bag in an eye. The system also includes an intraocular pseudophakic contact lens having a second optical lens and second haptics extending radially from the second optical lens and configured to contact the capsular bag in order to secure the intraocular pseudophakic contact lens against the artificial intraocular lens. The second optical lens includes a central portion and at least one annular portion surrounding the central portion, where the central and annular portions are configured to provide different optical powers.

In a third embodiment, an apparatus includes an intraocular pseudophakic contact lens having an optical lens and haptics extending radially from the optical lens and configured to contact a capsular bag in an eye in order to secure the intraocular pseudophakic contact lens against an artificial intraocular lens. The optical lens includes a central portion and at least one annular portion surrounding the central portion, where the central and annular portions are configured to provide different optical powers. Anterior surfaces of the haptics include capsular wall-engaging surfaces configured to contact an inner capsular wall surface at an anterior leaflet of the capsular bag, where the capsular wall-engaging surfaces are configured to promote confinement, capture, or attachment of the haptics. Posterior surfaces of the haptics include ridges configured to capture at least one edge of the artificial intraocular lens. The haptics are flexible such that outer portions of the haptics are configured to drive the ridges into the at least one edge of the artificial intraocular lens based on surface pressure from an anterior leaflet of the capsular bag against the outer portions of the haptics. The central portion of the optical lens is configured to provide a central optical magnification, and the at least one annular portion of the optical lens is configured to provide at least one different optical magnification or no optical magnification.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

FIGS. 1 through 13, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

This disclosure relates to devices, systems, and techniques for treating age-related macular degeneration (AMD) or other types of eye disorders using an intraocular pseudophakic contact lens (IOPCL) that can be mounted on, attached to, or otherwise secured to an artificial intraocular lens (IOL) for each of one or more eyes of a patient. The intraocular pseudophakic contact lens includes an optical lens having different regions with different optical powers (refractive powers). For instance, the central region of the optical lens may provide a first amount of optical magnification (such as a high plus power optical magnification), and at least one annular region of the optical lens around the central region may provide at least one different amount of optical magnification (or no optical magnification). Among other things, this approach can be used to deliver a customized treatment for early and intermediate-stage AMD in pseudophakic patients. These patients may, for instance, have lost sufficient vision to support keeping their driving privileges. They may have also actually lost their drivers' licenses and/or the ability to read normal print.

Figure 1:
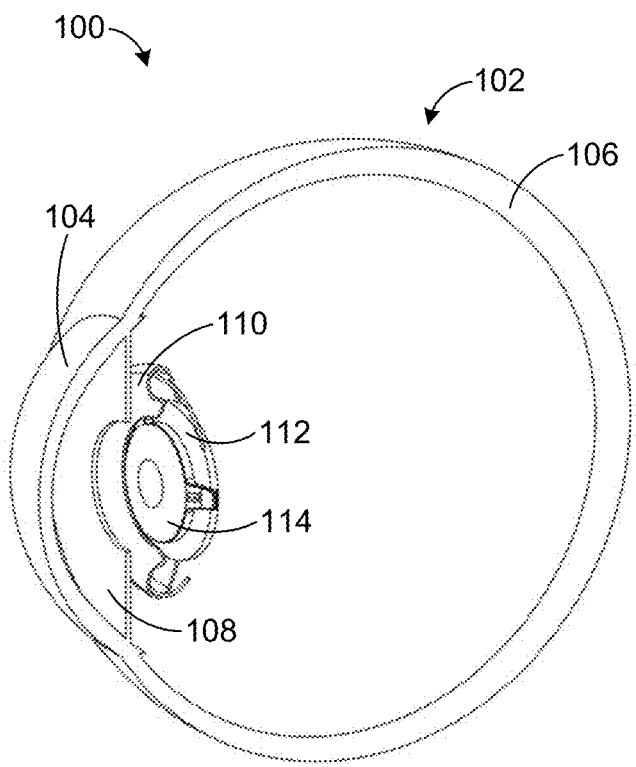
FIGS. 1 and 2 illustrate an example system for treating age-related macular degeneration (AMD) or other eye disorders according to this disclosure.
Figure 2:
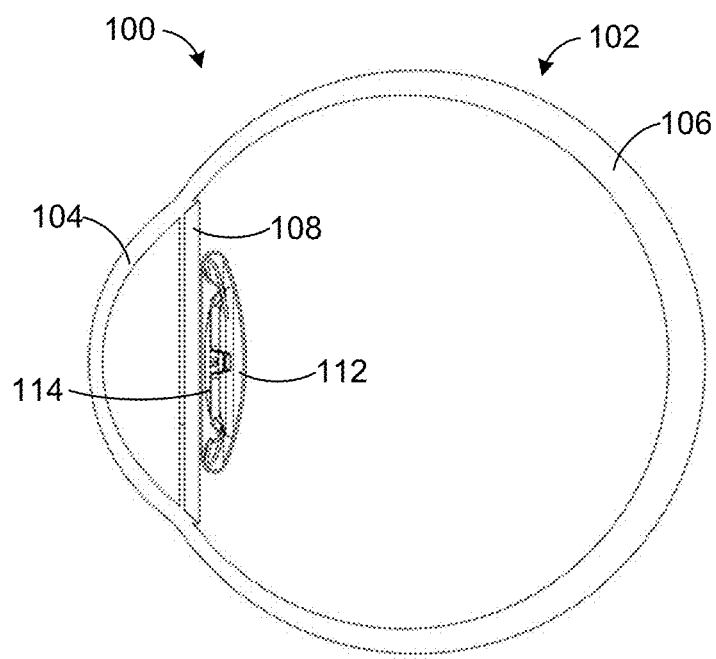

FIGS. 1 and 2 illustrate an example system 100 for treating AMD or other eye disorders according to this disclosure. As shown in FIGS. 1 and 2, the system 100 is used in conjunction with an eye 102 of a patient. Depending on the circumstances, a single system 100 may be used with one eye 102 of the patient, or two systems 100 may be used with both eyes 102 of the patient. The eye 102 generally includes a cornea 104, a sclera 106, and an iris 108. The eye 102 itself is shown in cross-sectional form in FIG. 1 for ease of illustration and explanation. The cornea 104 represents the clear front portion of the eye 102 through which light passes to enter into the eye 102. The sclera 106 represents the tough outer white portion of the eye 102. The iris 108 represents the component of the eye 102 that controls the size of the eye's pupil to thereby control the amount of light from the cornea 104 that enters into the interior of the eye 102.

The eye 102 also includes a capsular bag 110, which typically holds the natural crystalline lens of the eye 102. However, in this example, the natural crystalline lens has been removed and replaced with an artificial intraocular lens (IOL) 112. The intraocular lens 112 generally includes an optical lens and one or more haptics. The optical lens of the intraocular lens 112 receives light entering the eye 102 and focuses the light onto the retina of the eye 102. The haptics of the intraocular lens 112 help to hold the intraocular lens 112 within the capsular bag 110 so that the optical lens of the intraocular lens 112 is in a desired position within the eye. An eye 102 in which the natural crystalline lens has been replaced with an artificial intraocular lens 112 is often referred to as a "pseudophakic" eye. Note that there are a wide variety of artificial intraocular lenses that may be used in a patient, and additional artificial intraocular lenses are sure to be developed in the future. The intraocular lens 112 shown here is for illustration only, and any other suitable artificial intraocular lens now known or later developed may be used in the system 100. Also, the intraocular lens 112 may be used here to provide any desired optical correction or other modification of light passing through the eye 102.

An intraocular pseudophakic contact lens (IOPCL) 114 has been placed on or otherwise in front of the intraocular lens 112 (possibly without touching the uveal tissue). The intraocular pseudophakic contact lens 114 represents an additional lens that can be mounted on, attached to, or otherwise secured to the intraocular lens 112. As shown here, the intraocular pseudophakic contact lens 114 may be placed on or in front of the anterior surface of the intraocular lens 112, meaning the front surface of the intraocular lens 112 with respect to the eye 102. Light enters through the cornea 104 and passes through the pupil before entering the intraocular pseudophakic contact lens 114, which modifies the light. The modified light then passes through the optical lens of the intraocular lens 112 and is again modified. The twice-modified light then travels through the remainder of the eye 102 to reach the retina at the back of the eye 102.

As described below, the intraocular pseudophakic contact lens 114 includes an optical lens and optionally a mechanism for securing the intraocular pseudophakic contact lens 114 to or against the intraocular lens 112. In some embodiments, for example, the intraocular pseudophakic contact lens 114 includes one or more haptics that extend a short distance and fit under an anterior leaflet of the capsular bag 110 in the eye 102. This allows the haptics to be captured and confined by the anterior leaflet and possibly attach to the capsular wall of the anterior leaflet via fibrosis or re-fibrosis. The anterior leaflet represents the outer portion of the front side of the capsular bag 110 that remains after an opening (referred to as a capsulorhexis) is formed in the capsular bag 110 so that the natural crystalline lens can be removed. The insertion of the haptics of the intraocular pseudophakic contact lens 114 under the anterior leaflet helps to secure the intraocular pseudophakic contact lens 114 in place. In some cases, the healing process in the eye 102 can cause fibrosis or re-fibrosis to occur, which could also attach the anterior leaflet to the haptics of the intraocular pseudophakic contact lens 114. In other embodiments, the intraocular pseudophakic contact lens 114 includes one or more pins that can pierce the lens material of the intraocular lens 112. In still other embodiments, the intraocular pseudophakic contact lens 114 may be designed to mate with or otherwise connect to one or more components of the intraocular lens 112 specifically designed for use with the intraocular pseudophakic contact lens 114. In general, any suitable mechanism(s) may be used to mount, attach, or otherwise secure the intraocular pseudophakic contact lens 114 in place relative to the intraocular lens 112.

Depending on the implementation, the intraocular pseudophakic contact lens 114 may be multi-focal and include a combination of lens powers, such as a high plus power optical segment and at least one other optical segment with a different power or no power. The desired optical powers of the intraocular pseudophakic contact lens 114 may be achieved in any suitable manner. For example, in some embodiments, the optical powers of the intraocular pseudophakic contact lens 114 could be delivered by varying one or both of the anterior and posterior sides of the optic in the intraocular pseudophakic contact lens 114.

While often described as being used to treat both eyes 102 of a patient, this is not necessarily required. For instance, a single eye 102 of a patient may be treated using an intraocular pseudophakic contact lens 114. The other eye 102 of the patient may or may not include an intraocular pseudophakic contact lens 114, and there is no requirement that the other eye 102 include the same type of intraocular pseudophakic contact lens 114. In general, the approaches described here can be easily customized to provide desired correction(s) of each patient's eye(s) 102 individually or collectively.

Although FIGS. 1 and 2 illustrate one example of a system 100 for treating AMD or other eye disorders, various changes may be made to FIGS. 1 and 2. For example, any suitable intraocular pseudophakic contact lens 114 and any suitable intraocular lens 112 may be used in the eye 102.

Figure 3:
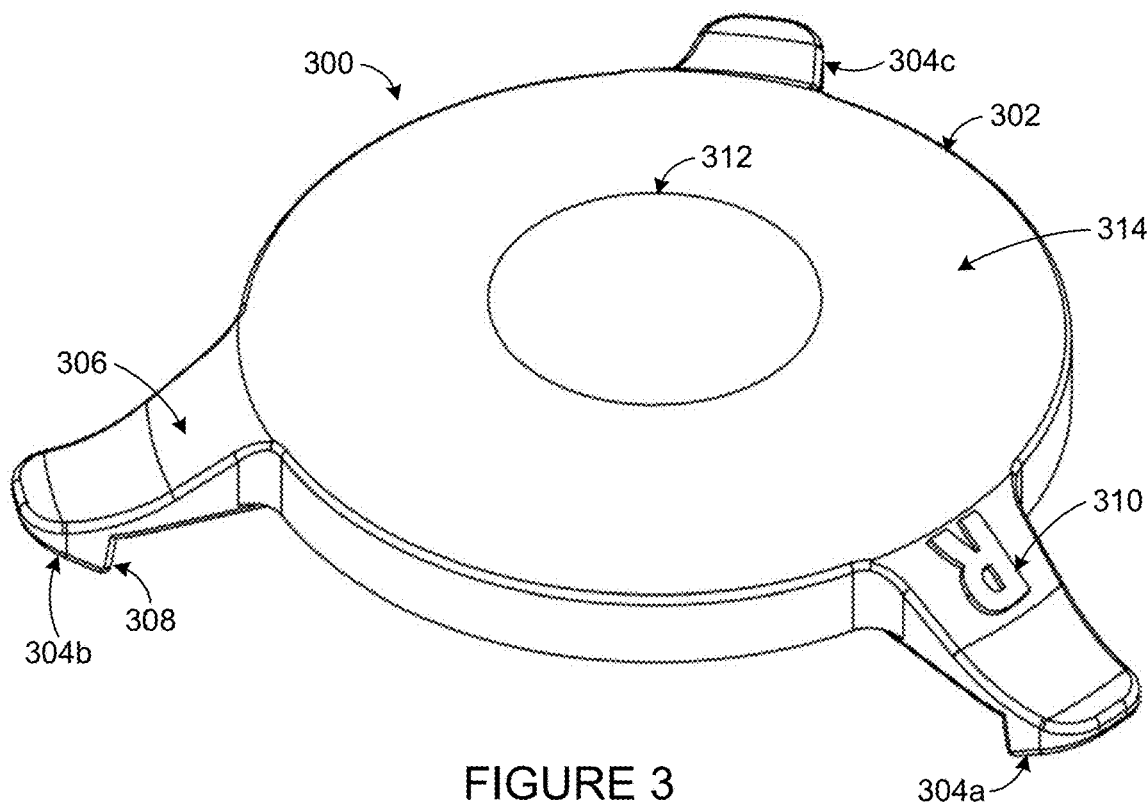
FIG. 3 illustrates a perspective view of an example intraocular pseudophakic contact lens for treating AMD or other eye disorders according to this disclosure.
Figure 4:
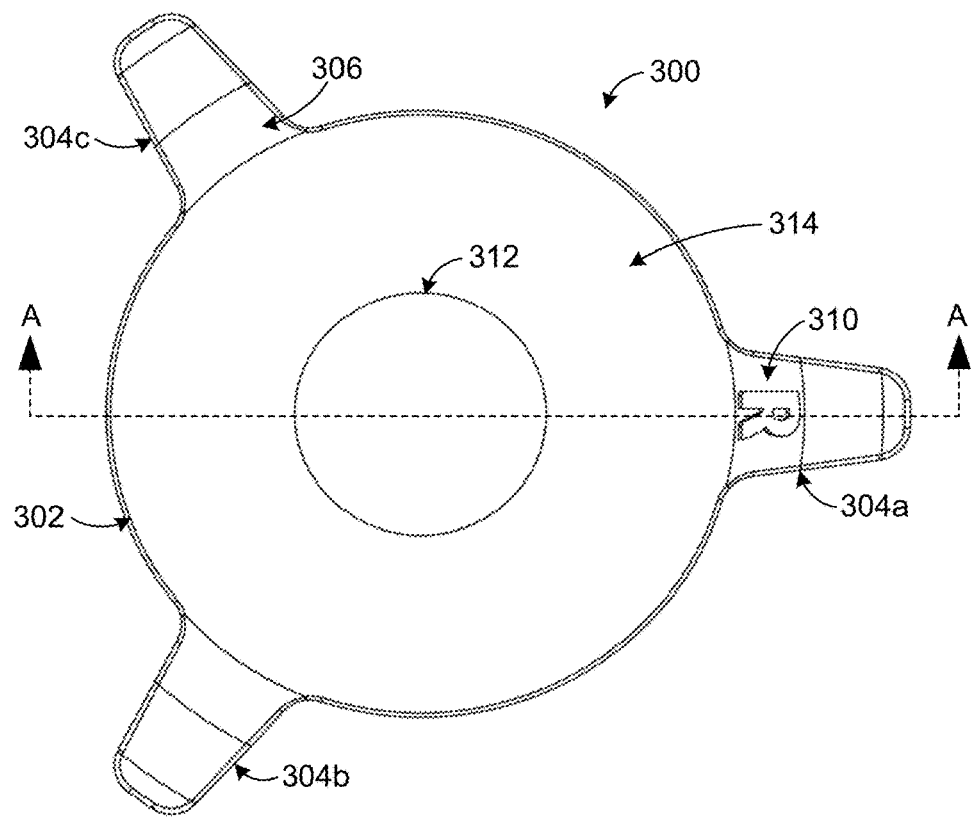
FIG. 4 illustrates a top view of an example intraocular pseudophakic contact lens for treating AMD or other eye disorders according to this disclosure.
Figure 5:
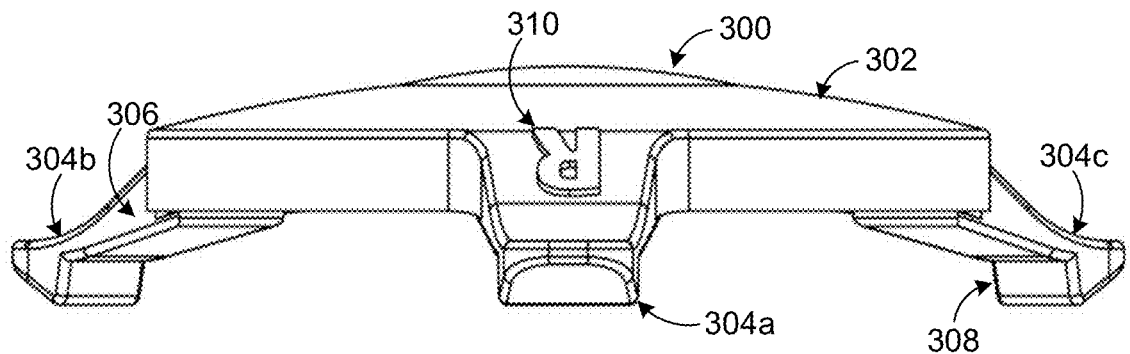
FIG. 5 illustrates a side view of an example intraocular pseudophakic contact lens for treating AMD or other eye disorders according to this disclosure.
Figure 6:
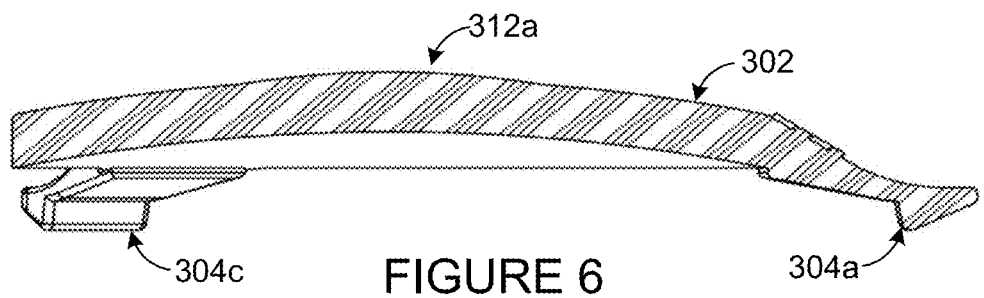
FIGS. 6 and 7 illustrate different cross-sectional views of an example intraocular pseudophakic contact lens for treating AMD or other eye disorders according to this disclosure.
Figure 7:
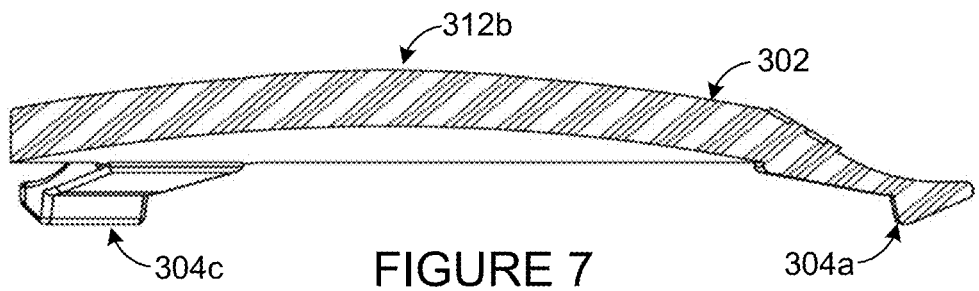

FIGS. 3 through 7 illustrate an example intraocular pseudophakic contact lens 300 for treating AMD or other eye disorders according to this disclosure. More specifically, FIG. 3 illustrates a perspective view of the intraocular pseudophakic contact lens 300, FIG. 4 illustrates a top view of the intraocular pseudophakic contact lens 300, and FIG. 5 illustrates a side view of the intraocular pseudophakic contact lens 300. FIGS. 6 and 7 illustrate different cross-sectional views of the intraocular pseudophakic contact lens 300. For ease of explanation, the intraocular pseudophakic contact lens 300 may be described as representing the intraocular pseudophakic contact lens 114 and as being used in the system 100 of FIGS. 1 and 2. However, the intraocular pseudophakic contact lens 300 may be used with any other suitable intraocular lens.

As shown in FIGS. 3 through 5, the intraocular pseudophakic contact lens 300 includes an optical lens 302, which denotes the portion of the intraocular pseudophakic contact lens 300 that alters light passing through the intraocular pseudophakic contact lens 300. For example, the light that passes through the optical lens 302 may then travel through an associated intraocular lens 112 before reaching the retina of a patient's eye 102. The optical lens 302 can be formed from any suitable material(s), such as silicone or acrylic. The optical lens 302 can also be formed in any suitable manner, such as by using a mold, laser, or lathe cut manufacturing process. Different optical lenses 302 in different intraocular pseudophakic contact lenses 300 can be designed and manufactured to provide different types of optical modifications, such as when different optical lenses 302 provide different amounts of optical magnification.

Multiple haptics 304a-304c extend from multiple sides of the optical lens 302. The haptics 304a-304c are sized and shaped so that they extend a short distance from the optical lens 302 and fit under the anterior leaflet of the capsular wall in a patient's eye 102 after implantation. Each haptic 304a-304c could be formed from any suitable material(s) and in any suitable manner. For example, each haptic 304a-304c could be formed from the same material(s) as the optical lens 302. Note that while three haptics 304a-304c are shown here, the intraocular pseudophakic contact lens 300 could include any number of haptics, including a single haptic. Also note that while the haptics 304a-304c angle downward (meaning the haptics 304a-304c generally extend outward and posteriorly from the optical lens 302), the haptics 304a-304c could have any other suitable arrangement. In addition, note that the haptics 304a-304c may be coupled to the optical lens 302 in any suitable manner, such as when the haptics 304a-304c are formed integral with the optical lens 302 or are attached to the optical lens 302 or to a retaining ring or other structure (integral with or attached to the optical lens 302) using adhesive or other suitable connecting mechanism.

Each of the haptics 304a-304c may include a textured surface 306, which may facilitate capture or confinement of the haptics 304a-304c by the anterior leaflet of the capsular wall in a patient's eye 102. Among other things, this can help the haptics 304a-304c to secure the intraocular pseudophakic contact lens 300 in place on or to the intraocular lens 112. In some cases, the textured surfaces 306 allow the haptics 304a-304c to actually physically bond to the anterior leaflet of the capsular wall in the patient's eye 102, such as through fibrosis or re-fibrosis during the healing process. In other cases, the textured surfaces 306 may simply resist movement of the haptics 304a-304c relative to the anterior leaflet of the capsular wall in the patient's eye 102.

Each textured surface 306 represents any suitable structure that facilitates confinement, capture, or attachment of the haptics 304a-304c by or to the anterior leaflet of the capsular wall. In some cases, each textured surface 306 may represent an electrical discharge machining (EDM) finish, or each textured surface 306 may represent holes formed partially or completely through the haptics 304a-304c (in which case the numbers and sizes of the holes in the textured surfaces 306 may vary as needed or desired). Note that other forms of texturing may be used here, or no texturing may be needed. Also note that the haptics 304a-304c may be omitted if not needed, such as when the intraocular pseudophakic contact lens 300 can be held in place on an intraocular lens 112 via surface tension, adhesive, or other technique. In addition, note that other types of haptics may be used with the intraocular pseudophakic contact lens 300, or pins embedded in or passing through projections from the optical lens of the intraocular pseudophakic contact lens 300 or other structures of the intraocular pseudophakic contact lens 300 may be used to secure the intraocular pseudophakic contact lens 300 to the intraocular lens 112. In general, this disclosure is not limited to any particular haptic design or mechanism for mounting or attaching the intraocular pseudophakic contact lens 300 on or to the intraocular lens 112.

In this example, the haptics 304a-304c of the intraocular pseudophakic contact lens 300 are formed as large projections that extend from the sides of the optical lens 302, effectively forming long "wings" extending from the optical lens 302. An inner portion of each haptic 304a-304c projects outward and downward (posteriorly) in this example, and an outer portion of each haptic 304a-304c projects outward and slightly upward in this example (although the outer portion of each haptic 304a-304c may be flexible as described below). Note, however, that other forms for the haptics 304a-304c could also be used. Each of the outer portions of the haptics 304a-304c has a thickness that tapers towards the outer edge of the haptic 304a-304c, which may facilitate easier insertion of the haptics 304a-304c under the anterior leaflet of the capsular wall in a patient's eye 102. The lower surfaces of the haptics 304a-304c also include ridges 308, and multiple ridges 308 of multiple haptics 304a-304c can be used to capture one or more edges of the underlying intraocular lens 112. This can help to center the intraocular pseudophakic contact lens 300 on the intraocular lens 112. This can also help to retain the intraocular pseudophakic contact lens 300 in place on the intraocular lens 112 during the healing process or otherwise during use. While the ridges 308 are shown here as being generally flat or slightly curved, the ridges 308 may incorporate other features. For instance, lips may be formed by small inward projections extending from the bottoms or other portion(s) of the ridges 308 inward towards a central optical axis of the optical lens 302 (meaning a vertical axis through the center of the optical lens 302 in FIG. 5).

The haptics 304a-304c may have any suitable positions in the intraocular pseudophakic contact lens 300. For example, in some embodiments, the haptics 304a-304c are evenly spaced about 120° apart. In other embodiments, the haptics 304a-304c are unevenly spaced, such as when the haptic 304a is separated from each of the haptics 304b-304c by about 125° and the haptics 304b-304c are separated from each other by about 110° (which may be based on, for instance, the positions of haptics of the intraocular lens 112 onto which the intraocular pseudophakic contact lens 300 will be placed). Also, in some cases, the intraocular pseudophakic contact lens 300 may be designed for implantation into a patient's eye 102 at a specific orientation, and at least one alignment marking 310 may be provided to identify proper orientation of the intraocular pseudophakic contact lens 300 in the eye 102. In this example, a single alignment marking 310 having the form of a raised letter "R" may be used, such as to identify the haptic 304a to be positioned on the right side of the intraocular lens 112 as the intraocular lens 112 within the eye 102 is viewed by a surgeon or other personnel. However, any other or additional alignment markings 310 or no alignment markings may be used here.

The optical lens 302 may have any suitable optical power(s) depending on the implementation. In this example, the optical lens 302 includes a first lens portion 312 and a second lens portion 314, where the two portions 312-314 of the optical lens 302 may provide different levels of optical magnification. For instance, the first lens portion 312 may provide a specified amount of magnification (such as a high plus power magnification), and the second lens portion 314 may provide a different amount of magnification or possibly little or no magnification. To provide a high plus power in this example, the anterior surface of the first lens portion 312 may be convex, and the posterior surface of the first lens portion 312 may be concave. The amount of high plus power magnification can be adjusted here by altering the shape of one or more of the anterior and posterior surfaces of the first lens portion 312. For instance, FIGS. 6 and 7 illustrate example cross-sections of the intraocular pseudophakic contact lens 300 taken along line A-A in FIG. 4, where different first lens portions 312a-312b are shown as having different shapes in their anterior surfaces. These different shapes allow the different first lens portions 312a-312b to provide different amounts of high plus power magnification. As a particular example, the lens portion 312a may provide an optical power of +11 diopters, and the lens portion 312b may provide an optical power of +5 diopters (although these are example values only).

As a result, the first lens portion 312 in the intraocular pseudophakic contact lens 300 can be used to provide a high amount of plus power optical magnification. This supports the use of the intraocular pseudophakic contact lens 300 in the system 100 to help treat conditions such as AMD or other vision loss related to retinal disease, where the magnification can help a patient perform tasks such as reading normal-sized print more easily or regaining his or her driving privileges. The second lens portion 314 in the intraocular pseudophakic contact lens 300 can be used to provide a different amount of optical magnification or no optical magnification. For instance, the anterior surface of the second lens portion 314 may be convex (with less convexity compared to the first lens portion 312), and the posterior surface of the second lens portion 314 may be concave.

In this particular example, the first lens portion 312 is generally circular and positioned centrally in the intraocular pseudophakic contact lens 300, and the second lens portion 314 is generally annular and surrounds the first lens portion 312. However, each lens portion 312 and 314 may have any other suitable size, shape, and position within the intraocular pseudophakic contact lens 300. In general, the sizes, shapes, and positions of the lens portions 312-314 can vary as needed or desired in order to provide the desired optical magnification(s).

The intraocular pseudophakic contact lens 300 shown in FIGS. 3 through 7 can be easily secured over an intraocular lens 112, such as by capturing and confining the haptics 304a-304c of the intraocular pseudophakic contact lens 300 using the anterior leaflet of the capsular wall in the eye 102. In some cases, this could also involve physical bonding of the haptics 304a-304c to the anterior leaflet of the capsular wall, such as via a fibrosis or re-fibrosis mechanism. Thus, in some embodiments, the intraocular pseudophakic contact lens 300 may not need to be designed to work specifically with particular structures of any specific intraocular lenses 112. Instead, the intraocular lens 112 being used with an intraocular pseudophakic contact lens 300 need not have any predefined structures that are provided for coupling to an intraocular pseudophakic contact lens 300. Rather, the intraocular pseudophakic contact lens 300 can simply be sized so that, when the intraocular pseudophakic contact lens 300 is placed on the intraocular lens 112, it can be secured in place through capture and confinement by (and possibly bonding with) the anterior leaflet of the capsular wall. This allows the intraocular pseudophakic contact lens 300 to be used with a wide variety of intraocular lenses 112, including different types of intraocular lenses 112 and including existing intraocular lenses 112 already implanted into patients. There is no need to remove an existing intraocular lens 112 from a patient in order to install a new intraocular lens and an intraocular pseudophakic contact lens. Note, however, that an intraocular pseudophakic contact lens may also be designed to specifically mate with a particular intraocular lens in other embodiments.

Moreover, the intraocular pseudophakic contact lens 300 could be easily removed from a patient's eyes 102, such as any suitable time after implantation or prior to bonding of the haptics 304a-304c to the capsular wall (assuming fibrosis or re-fibrosis holds the intraocular pseudophakic contact lens 300 in place). Among other things, this allows one intraocular pseudophakic contact lens 300 to be removed and replaced with a different intraocular pseudophakic contact lens 300 if a different optical magnification is needed or desired.

The intraocular pseudophakic contact lens 300 could have any suitable size, shape, and dimensions. For example, intraocular pseudophakic contact lenses 300 could be made available in a range of diameters from about 4 millimeters to about 6 millimeters. Also, the intraocular pseudophakic contact lenses 300 could be made available with varying base curvatures for their optical lenses 302. Of course, an intraocular pseudophakic contact lens 300 could also be custom designed for a particular patient's eye 102, such as when one or more specific curvatures are needed to provide a desired amount of optical magnification in the particular patient's eye 102.

In some embodiments, the intraocular pseudophakic contact lens 300 and various components of the intraocular pseudophakic contact lens 300 may have the following design parameters. The diameter of the first lens portion 312 may be about 1.8 millimeters, the diameter of the second lens portion 314 may be about 4.5 millimeters, the diameter of a circle defined by the ridges 308 may be about 6.05 millimeters, and the diameter of a circle defined by outer edges of the haptics 304a-304c may be about 7 millimeters. The straight edges of each haptic 304a-304c when viewed from the top may taper from a separation of about 0.97 millimeters to about 0.63 millimeters, where the straight edges define an angle of about 15°. The optical lens 302 may have a thickness along its outer edge of about 0.375 millimeters, and there may be a step of about 0.065 millimeters between the posterior surface of the optical lens 302 along its outer edge and posterior surfaces of the haptics 304a-304c. Each of the ridges 308 may form an angle of about 10° relative to a central optical axis of the optical lens 302, and the posterior surfaces of the haptics 304a-304c may extend from the optical lens 302 at an angle of about 103° relative to the central optical axis of the optical lens 302. The distance between the ridge 308 and the outer edge of each haptics 304a-304c may be about 0.48 millimeters. Various corners and edges of the intraocular pseudophakic contact lens 300 can be rounded, and the radii of curvatures of the anterior and posterior surfaces of the first and second lens portions 312-314 can vary based on the desired optical magnification(s) to be provided by the lens portions 312-314. Note, however, that these dimensions and other design parameters are for illustration only and can vary as needed or desired depending on the implementation of the intraocular pseudophakic contact lens 300.

The intraocular pseudophakic contact lens 300 can be implanted non-invasively in a patient's eye 102 and easily positioned on an intraocular lens 112. The implantation is non-invasive because the intraocular pseudophakic contact lens 300 is being installed on the anterior surface of an intraocular lens 112, which is typically easily accessible by a surgeon or other personnel during an implantation procedure. The implantation is also non-invasive because the intraocular pseudophakic contact lens 300 can be attached to the intraocular lens 112 without requiring attachment of the intraocular pseudophakic contact lens 300 to anatomical structures within the patient's eye 102, such as to the suculus of the patient's eye 102. The non-invasive implantation and easy positioning of an intraocular pseudophakic contact lens 300 provide a safe and effective surgical procedure to correct AMD or other eye disorders.

If the haptics 304a-304c of the intraocular pseudophakic contact lens 300 include ridges 308, the ridges 308 can be used to center the intraocular pseudophakic contact lens 300 on an underlying intraocular lens 112 as described above. If the intraocular pseudophakic contact lens 300 includes multiple haptics 304a-304c with associated ridges 308, the ridges 308 could help to perfectly center the intraocular pseudophakic contact lens 300 on the underlying intraocular lens 112. Such an approach allows the ridges 308 of the intraocular pseudophakic contact lens' haptics 304a-304c to capture the underlying intraocular lens 112 at the edge and perfectly line up the optical center of the intraocular pseudophakic contact lens' optic with the optical center of the intraocular lens 112. This alignment helps to reduce or avoid induced optical aberrations or induced prisms caused by optical center misalignment.

Note that in the above example, the intraocular pseudophakic contact lens 300 could possibly be designed so that only the haptics 304a-304c of the intraocular pseudophakic contact lens 300 extend under the anterior leaflet of the capsular wall in a patient's eye 102. This allows the haptics 304a-304c to be captured and confined by the anterior leaflet while leaving the optical lens 302 of the intraocular pseudophakic contact lens 300 free and generally unobscured by the surrounding tissue in the patient's eye 102.

Also note that, in some embodiments, the surgical tool disclosed in U.S. Patent Application Publication No. 2019/0269555 A1 (which is hereby incorporated by reference in its entirety) may be used to help implant an intraocular pseudophakic contact lens 300. For example, this tool may be used to separate at least part of the anterior leaflet of a patient's eye 102 from an implanted intraocular lens 112, allowing haptics 304a-304c of the intraocular pseudophakic contact lens 300 to be inserted between the anterior leaflet and the intraocular lens 112. As another example, this tool may be used to separate the anterior leaflet of a patient's eye 102 from an implanted intraocular pseudophakic contact lens, allowing the intraocular pseudophakic contact lens to be removed (and possibly replaced).

Although FIGS. 3 through 7 illustrate one example of an intraocular pseudophakic contact lens 300 for treating AMD or other eye disorders, various changes may be made to FIGS. 3 through 7. For example, the intraocular pseudophakic contact lens 300 could include any suitable number of each component shown in the figures. As a particular example, while the optical lens 302 is shown as having two portions 312 and 314, the optical lens 302 may have more than two regions (such as two or more annular regions around the central region). Also, the forms of the haptics 304a-304c shown here are examples only, and any other suitable structures or other mechanisms could be used to secure the intraocular pseudophakic contact lens 300 in place. Further, a number of other features could be used at one or more locations of the intraocular pseudophakic contact lenses 300. For instance, one or more drug-eluting materials could be placed on top, side, or bottom surfaces of the optical lenses in the intraocular pseudophakic contact lenses. Moreover, the specific dimensions, diopters, optical powers, and other values described above are for illustration only and do not limit this disclosure to the specific values.

In addition, the intraocular pseudophakic contact lens 300 shown in FIGS. 3 through 7 represents one example of the type of intraocular device that may be designed or modified for use in the system 100. However, various other intraocular devices may be designed or modified for use in the system 100. For example, U.S. Patent Application Publication No. 2020/0121446 A1 and U.S. Patent Application Publication No. 2019/0076237 A1 (both of which are hereby incorporated by reference in their entirety) disclose a number of intraocular pseudophakic contact lenses that include (or may be modified to include) optical lenses providing a central high plus power optical magnification, which would allow those intraocular pseudophakic contact lenses to be used in the system 100. Among other things, the intraocular pseudophakic contact lenses disclosed in the documents incorporated by reference above use pins, haptic loops, or other structures to secure the intraocular pseudophakic contact lenses to intraocular lenses, and any of these structures may be used with an intraocular pseudophakic contact lens as described above.

Figure 8:
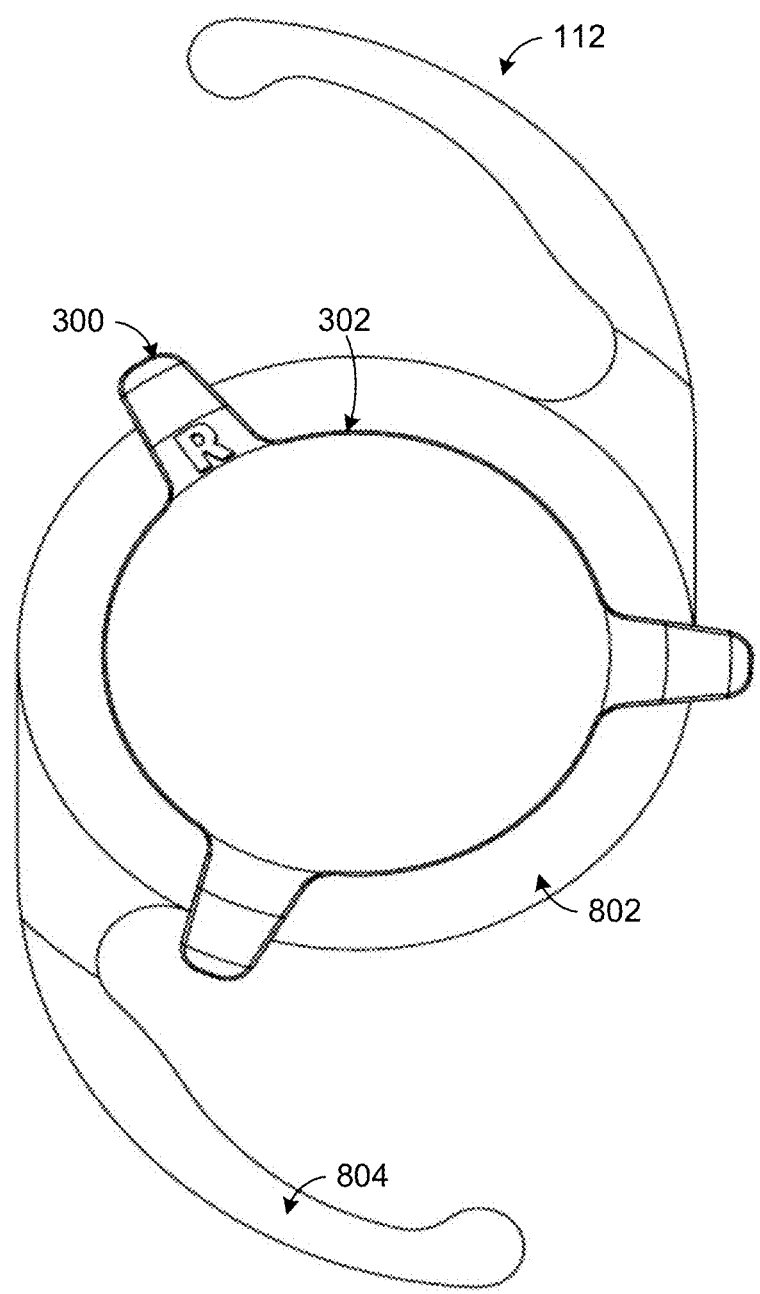
FIGS. 8 and 9 illustrate an example combination of an intraocular pseudophakic contact lens and an artificial intraocular lens that may be used for treating AMD or other eye disorders according to this disclosure.
Figure 9:
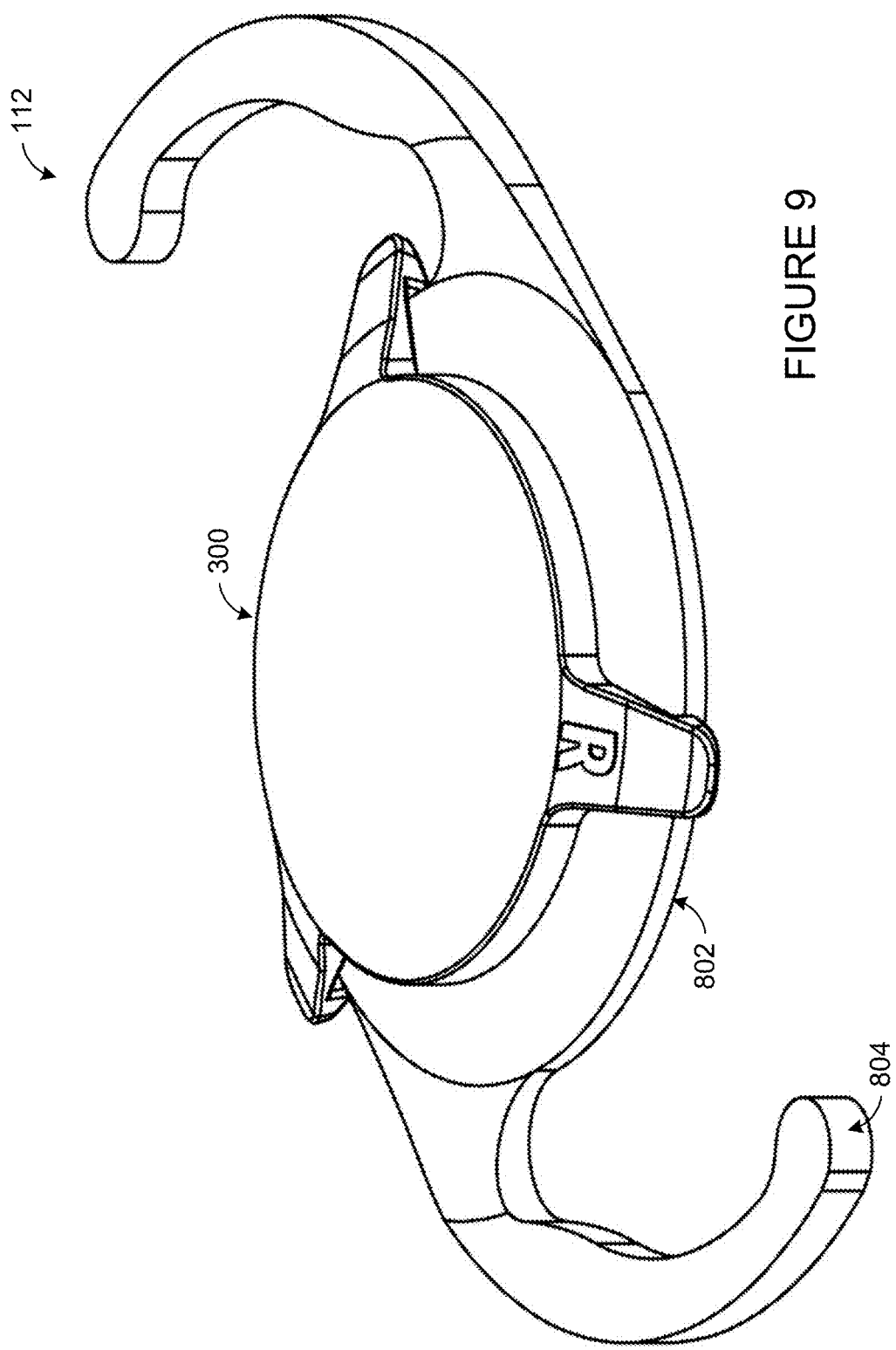

FIGS. 8 and 9 illustrate an example combination of an intraocular pseudophakic contact lens 300 and an artificial intraocular lens 112 that may be used for treating AMD or other eye disorders according to this disclosure. For ease of explanation, the combination may be described as being used in the system 100 of FIGS. 1 and 2. However, the system may use any other suitable combination of an intraocular pseudophakic contact lens and an intraocular lens.

As shown in FIGS. 8 and 9, the intraocular lens 112 includes an optical lens 802 and haptics 804 extending from the optical lens 802. The optical lens 802 receives light that has passed through the optical lens 302 of the intraocular pseudophakic contact lens 300 and focuses the light onto the retina of the eye 102. The haptics 804 help to hold the intraocular lens 112 within the capsular bag 110 so that the optical lens 802 is in a desired position within the eye 102. Note that the forms of the optical lens 802 and the haptics 804 shown here are examples only and that other intraocular lens may include different optical lenses or different haptics. For instance, the haptics of the intraocular lens 112 in FIGS. 1 and 2 take the form of loops rather than arms as in FIGS. 8 and 9.

Figure 10:
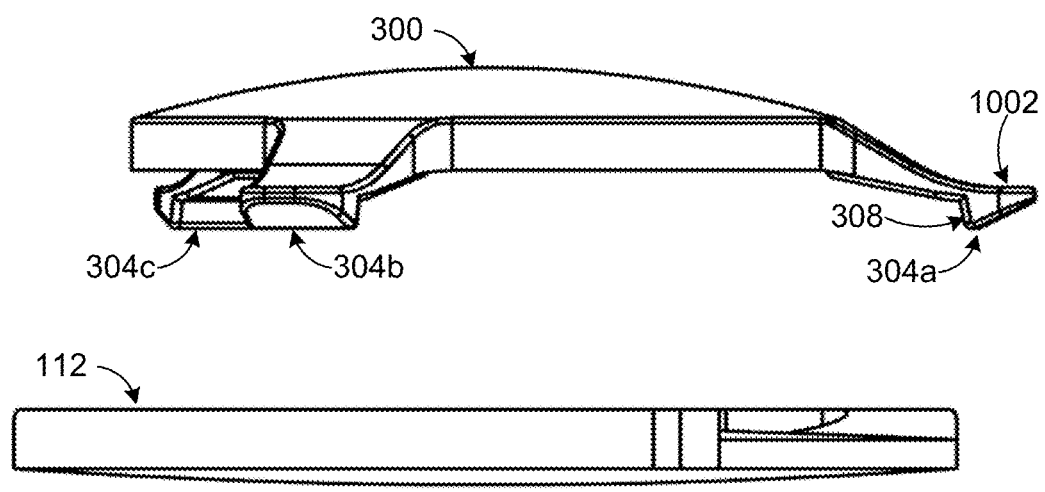
FIGS. 10 through 12 illustrate an example coupling of an intraocular pseudophakic contact lens to an artificial intraocular lens for treating AMD or other eye disorders according to this disclosure.
Figure 11:
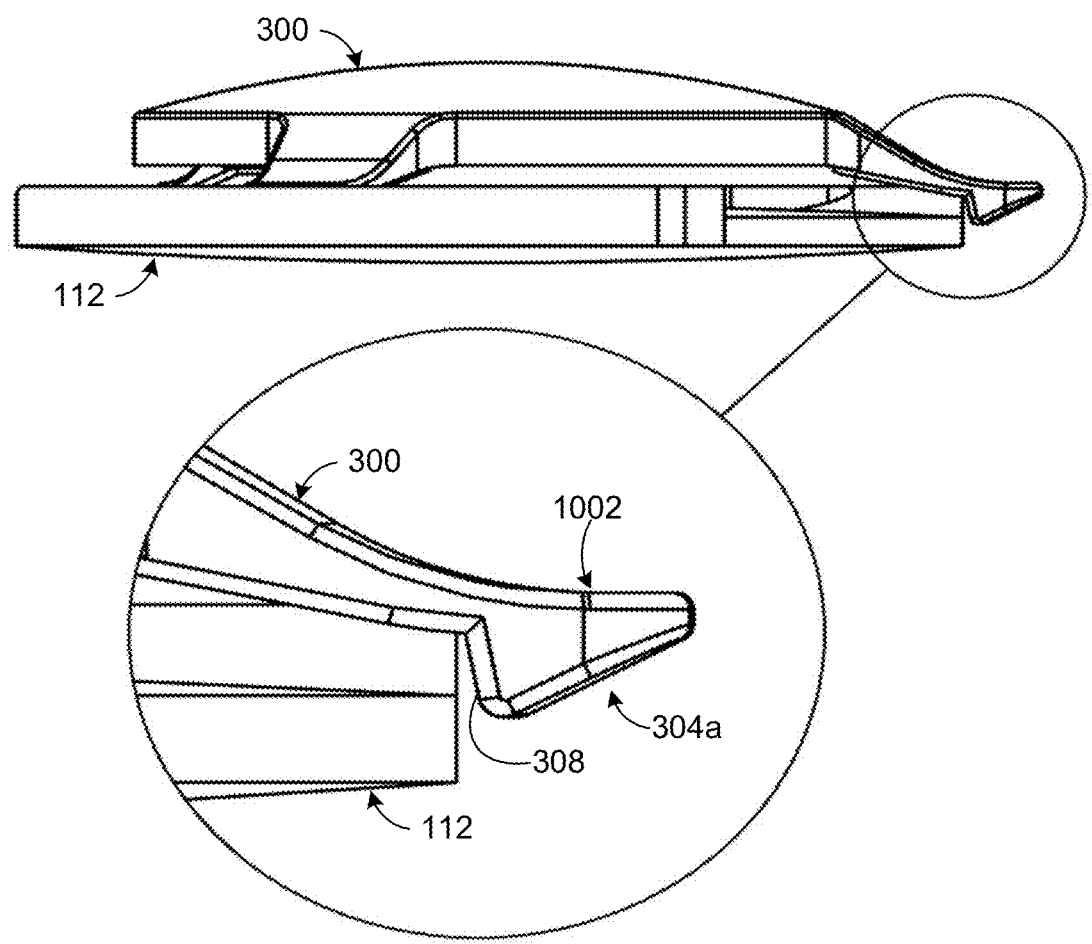
Figure 12:
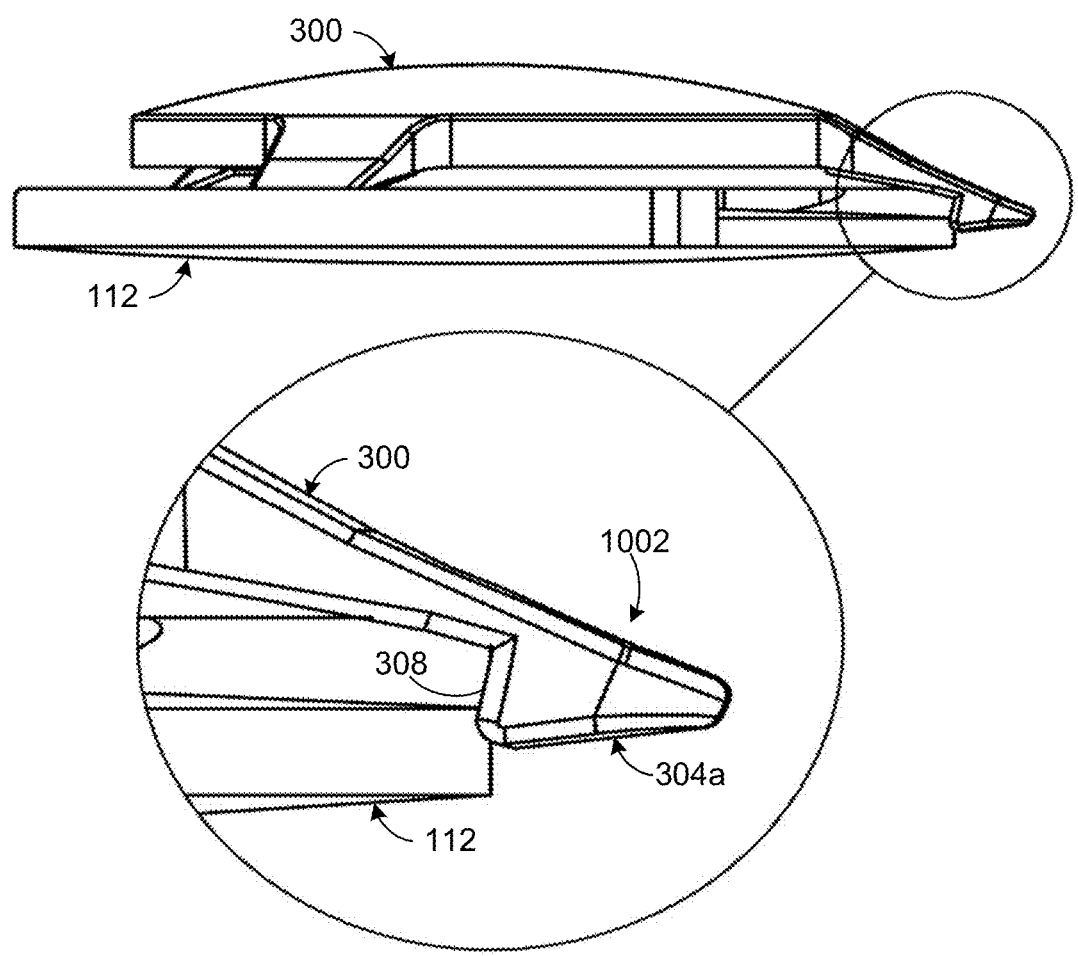

FIGS. 10 through 12 illustrate an example coupling of an intraocular pseudophakic contact lens 300 to an artificial intraocular lens 112 for treating AMD or other eye disorders according to this disclosure. For ease of explanation, the coupling may be described as being performed to help form the system 100 of FIGS. 1 and 2. However, the coupling may involve any other suitable intraocular pseudophakic contact lens and any other suitable intraocular lens.

As shown in FIG. 10, the intraocular pseudophakic contact lens 300 and the intraocular lens 112 are shown in side profile, and the intraocular pseudophakic contact lens 300 is being moved towards the intraocular lens 112. An outer portion 1002 of each haptic 304a-304c angles partially upward here, which facilitates coupling of the intraocular pseudophakic contact lens 300 to the intraocular lens 112 as described below. The intraocular pseudophakic contact lens 300 can be moved towards the intraocular lens 112 in any suitable manner, such as when a surgeon or other personnel uses a tool to grasp and manipulate the intraocular pseudophakic contact lens 300.

As shown in FIG. 11, the intraocular pseudophakic contact lens 300 is being placed onto the anterior surface of the intraocular lens 112. However, in FIG. 11, it is assumed that the outer portions 1002 of the haptics 304a-304c have not been placed under the anterior leaflet in the eye 102, which is why the outer portions 1002 of the haptics 304a-304c still angle partially upward here. This allows the ridges 308 of the haptics 304a-304c to more easily surround and capture the outer edge of the optical lens 802 of the intraocular lens 112.

As shown in FIG. 12, the intraocular pseudophakic contact lens 300 has now been secured to the anterior surface of the intraocular lens 112. In FIG. 12, it is assumed that the outer portions 1002 of the haptics 304a-304c have been placed under the anterior leaflet in the eye 102. The anterior leaflet applies a downward force to the outer portions 1002 of the haptics 304a-304c. Assuming the haptics 304a-304c are flexible, this surface pressure causes the outer portions 1002 of the haptics 304a-304c to deflect and angle partially downward, which helps to drive the ridges 308 (and optionally any lips or other structures on the ridges 308) into the outer edge of the optical lens 802 of the intraocular lens 112. This helps to secure the intraocular pseudophakic contact lens 300 to the intraocular lens 112 and helps to align the optical axes of the intraocular pseudophakic contact lens 300 and the intraocular lens 112.

Although FIGS. 8 and 9 illustrate one example of a combination of an intraocular pseudophakic contact lens 300 and an artificial intraocular lens 112 that may be used to treat AMD or other eye disorders and FIGS. 10 through 12 illustrate one example of a coupling of an intraocular pseudophakic contact lens 300 to an artificial intraocular lens 112 to treat AMD or other eye disorders, various changes may be made to FIGS. 8 through 12. For example, any other suitable mechanism (possibly including just surface tension) may be used to hold the intraocular pseudophakic contact lens on or against the intraocular lens.

Figure 13:
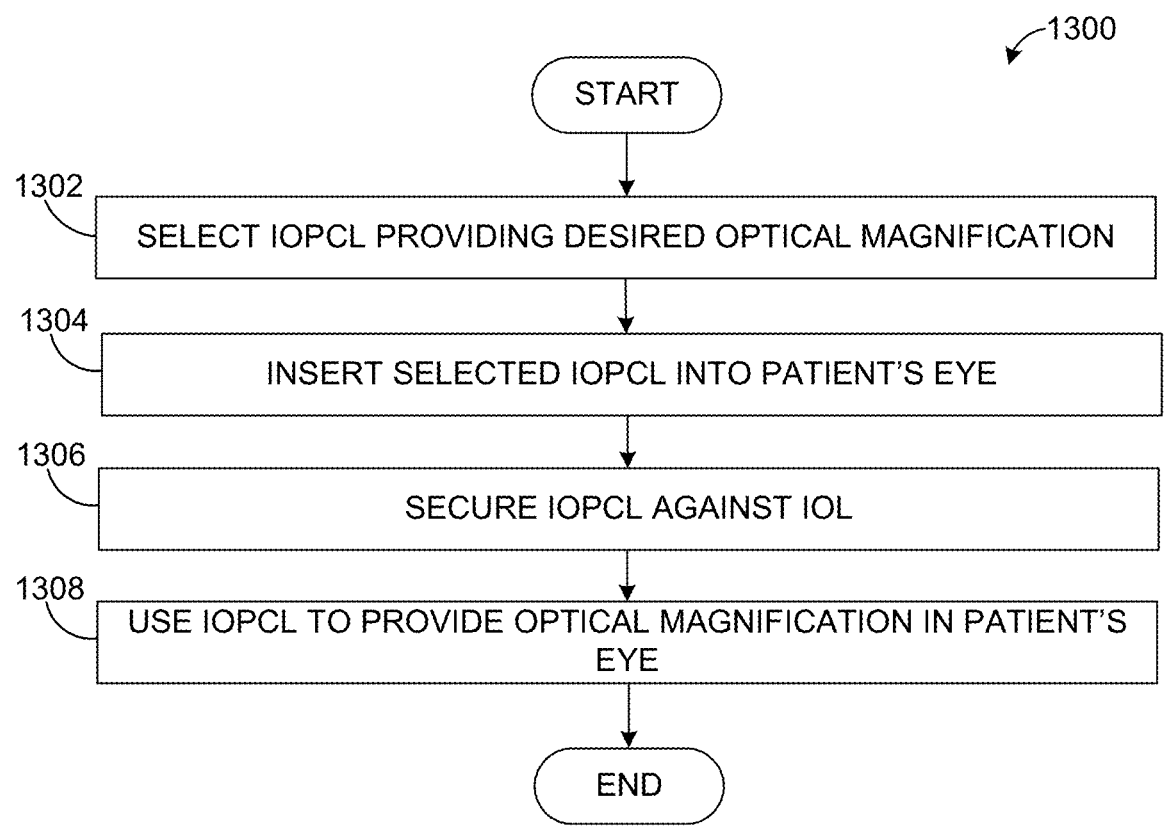
FIG. 13 illustrates an example method for treating AMD or other eye disorders according to this disclosure.

FIG. 13 illustrates an example method 1300 for treating AMD or other eye disorders according to this disclosure. For ease of explanation, the method 1300 is described as using the intraocular pseudophakic contact lens 300 as part of the formation of the system 100. However, the method 1300 may use any other suitable intraocular pseudophakic contact lens.

As shown in FIG. 13, an intraocular pseudophakic contact lens (IOPCL) providing a desired amount of optical magnification is selected at step 1302 and inserted into a patient's eye at step 1304. This may include, for example, a surgeon or other personnel selecting an intraocular pseudophakic contact lens 300 that provides a desired amount of high plus power optical magnification, such as from a kit. This may also include the surgeon or other personnel forming a small incision in the patient's eye 102 and inserting the intraocular pseudophakic contact lens 300 into the eye 102 through the incision. The intraocular pseudophakic contact lens 300 can be rolled, folded, or otherwise reduced in cross-sectional size in order to insert the intraocular pseudophakic contact lens 300 through a smaller incision.

The intraocular pseudophakic contact lens is secured against an intraocular lens in the patient's eye at step 1306. In some embodiments, this may include, for example, one or more haptics 304a-304c of the intraocular pseudophakic contact lens 300 sliding or otherwise being inserted under the anterior leaflet of the capsular wall in the patient's eye 102. In other embodiments, this may include one or more pins of the intraocular pseudophakic contact lens 300 piercing the lens material of the optical lens 802 in the intraocular lens 112. Any other suitable mechanism may be used here to secure the intraocular pseudophakic contact lens 300 against the intraocular lens 112. The intraocular pseudophakic contact lens is used to provide optical magnification in the patient's eye at step 1308. This may include, for example, the first lens portion 312 of the intraocular pseudophakic contact lens 300 providing high plus power magnification during use of the intraocular pseudophakic contact lens 300.

Although FIG. 13 illustrates one example of a method 1300 for treating AMD or other eye disorders, various changes may be made to FIG. 13. For example, while shown as a series of steps, various steps in FIG. 13 could overlap, occur in parallel, occur in a different order, or occur any number of times.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in this patent document should not be read as implying that any particular element, step, or function is an essential or critical element that must be included in the claim scope. Also, none of the claims is intended to invoke 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," "processing device," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
    an intraocular pseudophakic contact lens comprising:
        an optical lens; and
        haptics extending radially from the optical lens and configured to contact a capsular bag in an eye in order to secure the intraocular pseudophakic contact lens against an artificial intraocular lens;
    wherein the optical lens comprises a central portion and at least one annular portion surrounding the central portion, the central and annular portions configured to provide different optical powers;
    wherein anterior surfaces of the haptics comprise capsular wall-engaging surfaces configured to contact an inner capsular wall surface at an anterior leaflet of the capsular bag, the capsular wall-engaging surfaces configured to promote confinement, capture, or attachment of the haptics;
    wherein posterior surfaces of the haptics comprise ridges configured to capture at least one edge of the artificial intraocular lens; and
    wherein the haptics are flexible such that outer portions of the haptics are configured to drive the ridges into the at least one edge of the artificial intraocular lens based on surface pressure from the anterior leaflet of the capsular bag against the outer portions of the haptics.

2. The apparatus of claim 1, wherein:
    the central portion of the optical lens is configured to provide a central optical magnification; and
    the at least one annular portion of the optical lens is configured to provide no optical magnification.

3. The apparatus of claim 2, wherein:
    the central portion of the optical lens comprises a convex anterior surface and a concave posterior surface; and
    each annular portion of the optical lens comprises a convex anterior surface and a concave posterior surface.

4. The apparatus of claim 1, wherein one of the haptics comprises an alignment marking identifying a desired orientation of the intraocular pseudophakic contact lens in the eye.

5. The apparatus of claim 1, wherein the central portion of the optical lens is configured to provide an optical power of about +5 diopters to about +11 diopters.

6. The apparatus of claim 1, wherein:
    the central portion of the optical lens is configured to provide a central optical magnification; and
    the at least one annular portion of the optical lens is configured to provide at least one different optical magnification.

7. The apparatus of claim 6, wherein:
    the central portion of the optical lens comprises a convex anterior surface and a concave posterior surface; and
    each annular portion of the optical lens comprises a convex anterior surface and a concave posterior surface.

8. The apparatus of claim 7, wherein a convexity of the convex anterior surface of the central portion is greater than a convexity of the convex anterior surface of each annular portion.

9. The apparatus of claim 1, wherein the haptics comprise three haptics configured to center the intraocular pseudophakic contact lens on the artificial intraocular lens.

10. A system comprising:
    an artificial intraocular lens comprising a first optical lens and first haptics configured to be implanted within a capsular bag in an eye; and
    an intraocular pseudophakic contact lens comprising:
        a second optical lens; and
        second haptics extending radially from the second optical lens and configured to contact the capsular bag in order to secure the intraocular pseudophakic contact lens against the artificial intraocular lens;
    wherein the second optical lens comprises a central portion and at least one annular portion surrounding the central portion, the central and annular portions configured to provide different optical powers;
    wherein anterior surfaces of the second haptics comprise capsular wall-engaging surfaces configured to contact an inner capsular wall surface at an anterior leaflet of the capsular bag, the capsular wall-engaging surfaces configured to promote confinement, capture, or attachment of the second haptics;
    wherein posterior surfaces of the second haptics comprise ridges configured to capture at least one edge of the artificial intraocular lens; and
    wherein the second haptics are flexible such that outer portions of the second haptics are configured to drive the ridges into the at least one edge of the artificial intraocular lens based on surface pressure from the anterior leaflet of the capsular bag against the outer portions of the second haptics.

11. The system of claim 10, wherein:
    the central portion of the second optical lens is configured to provide a central optical magnification; and
    the at least one annular portion of the second optical lens is configured to provide no optical magnification.

12. The system of claim 11, wherein:
the central portion of the second optical lens comprises a convex anterior surface and a concave posterior surface; and
each annular portion of the second optical lens comprises a convex anterior surface and a concave posterior surface.

13. The system of claim 10, wherein one of the second haptics comprises an alignment marking identifying a desired orientation of the intraocular pseudophakic contact lens in the eye.

14. The system of claim 10, wherein the central portion of the second optical lens is configured to provide an optical power of about +5 diopters to about +11 diopters.

15. The system of claim 10, wherein:
the central portion of the second optical lens is configured to provide a central optical magnification; and
the at least one annular portion of the second optical lens is configured to provide at least one different optical magnification.

16. The system of claim 15, wherein:
the central portion of the second optical lens comprises a convex anterior surface and a concave posterior surface; and
each annular portion of the second optical lens comprises a convex anterior surface and a concave posterior surface.

17. The system of claim 16, wherein a convexity of the convex anterior surface of the central portion is greater than a convexity of the convex anterior surface of each annular portion.

18. The system of claim 10, wherein the second haptics comprise three haptics configured to center the intraocular pseudophakic contact lens on the artificial intraocular lens.

19. The system of claim 10, wherein the second haptics are shorter than the first haptics.

20. An apparatus comprising:
an intraocular pseudophakic contact lens comprising:
an optical lens; and
haptics extending radially from the optical lens and configured to contact a capsular bag in an eye in order to secure the intraocular pseudophakic contact lens against an artificial intraocular lens;
wherein the optical lens comprises a central portion and at least one annular portion surrounding the central portion, the central and annular portions configured to provide different optical powers;
wherein anterior surfaces of the haptics comprise capsular wall-engaging surfaces configured to contact an inner capsular wall surface at an anterior leaflet of the capsular bag, the capsular wall-engaging surfaces configured to promote confinement, capture, or attachment of the haptics;
wherein posterior surfaces of the haptics comprise ridges configured to capture at least one edge of the artificial intraocular lens;
wherein the haptics are flexible such that outer portions of the haptics are configured to drive the ridges into the at least one edge of the artificial intraocular lens based on surface pressure from the anterior leaflet of the capsular bag against the outer portions of the haptics;
wherein the central portion of the optical lens is configured to provide a central optical magnification; and
wherein the at least one annular portion of the optical lens is configured to provide at least one different optical magnification or no optical magnification.

* * * * *